(12) United States Patent
Sadowski et al.

(10) Patent No.: US 7,009,186 B2
(45) Date of Patent: Mar. 7, 2006

(54) METHOD FOR MONITORING OF POLYMER IN LIQUID STATE

(75) Inventors: Janusz Sadowski, Tampere (FI); Jyrki Salminen, Porvoo (FI); Peter Huber, Bad Homburg (DE); Camie Heffels, Gernsheim (DE); Marian Mours, Weisenheim am Sand (DE); Klaus Reindel, Hassloch (DE); Jürgen Ettmüller, Hassloch (DE)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 0 days.

(21) Appl. No.: 10/250,575

(22) PCT Filed: Jan. 3, 2002

(86) PCT No.: PCT/FI02/00002

§ 371 (c)(1),
(2), (4) Date: Nov. 24, 2003

(87) PCT Pub. No.: WO02/054047

PCT Pub. Date: Jul. 11, 2002

(65) Prior Publication Data

US 2004/0070752 A1    Apr. 15, 2004

(30) Foreign Application Priority Data

Jan. 3, 2001    (FI) ................................ 20010010

(51) Int. Cl.
*G01N 21/88*    (2006.01)
(52) U.S. Cl. .................................... 250/373; 356/237.1
(58) Field of Classification Search ................ 250/373, 250/223
See application file for complete search history.

(56) References Cited

U.S. PATENT DOCUMENTS

| 35,868 A | * | 7/1862 | Kosaka ................... 292/307 R |
| 4,529,306 A | | 7/1985 | Kilham et al. |
| 4,888,484 A | * | 12/1989 | Harvey ....................... 250/343 |
| 4,902,137 A | | 2/1990 | Krieg et al. |
| 5,383,776 A | | 1/1995 | Trail et al. |
| 5,428,441 A | * | 6/1995 | Ogino et al. .................. 356/73 |
| 5,495,333 A | * | 2/1996 | Konda et al. ................ 356/339 |
| 5,684,583 A | | 11/1997 | Abe et al. |

FOREIGN PATENT DOCUMENTS

| EP | 0599297 | 6/1994 |
| EP | 0676632 | 10/1995 |
| EP | 0938961 | 9/1999 |
| JP | 59040146 | 3/1984 |
| WO | 99/14591 | 3/1999 |

* cited by examiner

*Primary Examiner*—David Porta
*Assistant Examiner*—Marcus Taningco
(74) *Attorney, Agent, or Firm*—Venable LLP; Eric J. Franklin

(57) ABSTRACT

In a method for monitoring of polymer in a liquid state, such as a polymer melt or resin, to detect inhomogeneities therein, such as the presence of other phase objects, especially gels in a matrix formed of the liquid state, the polymer in a liquid state flowing past an inspection point is monitored. At the inspection point, electromagnetic radiation in the form of UV light or polarised electromagnetic radiation is passed through the flow chamber (1) and received by a detector (8), and the absorption of the UV light or the changes in the state of polarisation of the electromagnetic radiation caused by the inhomogeneities are used to observe them.

15 Claims, 3 Drawing Sheets

METHOD FOR MONITORING OF POLYMER IN LIQUID STATE

FIELD OF THE INVENTION

The present invention relates to a method for monitoring of polymer in liquid state to detect inhomogeneities.

BACKGROUND OF THE INVENTION

Heterogeneities in polymers constitute a potential serious threat to the quality of plastic products. Incompletely dispersed additives, impurities from polymerisation or compounding, spatial variation in molar mass and gel particles are a few examples of heterogeneities. For example for polyethylene and other polyolefins, gel particles are considered to be the major cause for problems with processing and the quality of end products. Gels can be classified into three basic categories:

crosslinked gels (unmeltable molecular structure)
    rheological gels (meltable, but apparent because of significant differences in molecular structure)
    phase separation gels (copolymer differences in molecular structure, i.e. domains of homopolymer in copolymer melt)

The above-mentioned types are detectable by conventional methods.

Existence of crosslinked gel may be due to thermal oxidation and in such case its elemental composition will be different from the surrounding matrix polymer. This type is referred to as oxidised gel particles. A gel particle can also be formed in the polymerisation process and in this case it will have the same molecular composition as the matrix polymer, but a higher molar mass. This type is referred to as unoxidised gel particles. The detection of this last-mentioned type is difficult.

In order to speed-up quality control in the manufacturing process, gel particles should be detected already in the liquid (molten) state. Oxidised gel particles can be detected by optical microscopy because of their different material properties, and thus also refractive index or absorption properties different from the surrounding matrix phase.

Oxidation products absorb in the UV-range and also UV-microscopy can be used for their detection. On the other hand, unoxidised gel particles in a quiescent melt cannot be detected (visualised) by either classical optical or UV-microscopy, nor by spectroscopic methods, because they have the same elemental composition (refractive index) and the same repeating unit structure (spectroscopic properties) as the matrix polymer.

SUMMARY OF THE INVENTION

It is the purpose of the present invention to provide a method where other phase objects, such as gels, could be detected at an early stage in a liquid state polymer, such as a polymer melt or resin.

The invention utilises the fact that plastic materials in general, so also gels in particular, are built from chain molecules, thus they can change state of polarisation of light passing through the material. Even in the case of unoxidised gels, which have the same molecular composition, their chain structure and orientation is different than the matrix (they can be longer, have side chains, or can be differently bent or entangled), and thus they affect state of polarisation of light differently than the matrix does.

Differences in the state of polarisation between polymer matrix and gel can be optically visualised if the stream of molten plastic is placed between two crossed polarisers. Contrast enhancement of gels can also be achieved by adding two quarter-wave plates (λ/4) between the polarisers, thus transmitting circularly polarised light through the flow of polymer melt.

The invention makes it possible to visualize different areas in a polymer in liquid state which has not undergone solidification nor one-dimensionally oriented, and in general is still in an original free flowing state before any exposure to air or cooling that would change its material or mechanical properties.

BRIEF DESCRIPTION OF THE DRAWINGS

The invention will be explained in more detail in the following description of preferred embodiments as illustrated by way of example in the accompanying drawings, in which.

DETAILED DESCRIPTION OF THE PREFERRED EMBODIMENTS

Figure 1A:
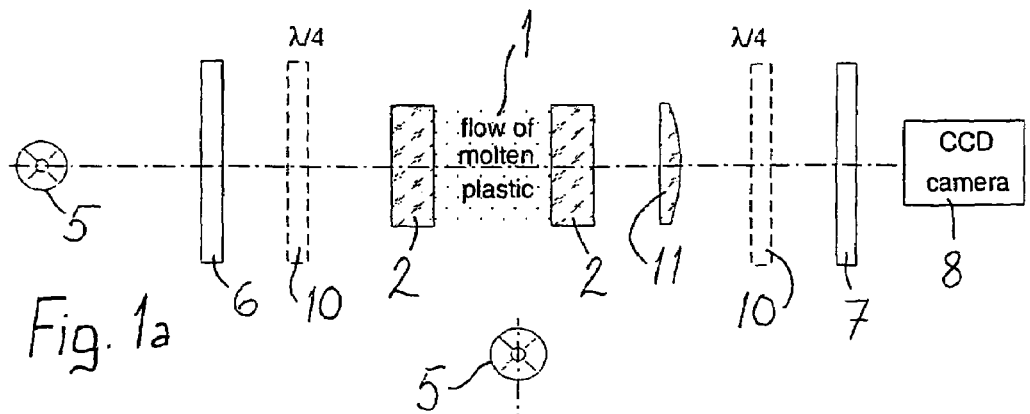
FIGS. 1a and 1b show two alternative arrangements of the first embodiment of the invention.

The invention can be realised in an on-line form either by constructing a flow chamber 1 with two windows 2 on the opposite sides (FIG. 1a), or with one window 2 and a mirror 3 in front of it (FIG. 1b) by using a semi-transparent mirror 4. In both alternatives, light coming from a light source 5 travels through a polariser 6, and after the polarised light has passed across the flow chamber 1 and has thereby traversed the polymer melt flowing along the flow chamber 1, it travels through a second polariser, analyser 7, that can be rotated. The light that has passed the analyser 7 is received by a detector 8, such as a CCD camera. The second configuration according to FIG. 1b could be preferable for two reasons: a) light is travelling twice through the gel, thus amplifying differences in the state of polarisation of light, and b), the whole optical part of the instrument can be mounted on one side of the flow chamber 1, such as flow channel of an extruder or a polymer melt processing apparatus of another kind. This is more practical for application in an industrial environment.

Figures 2A, 2B:
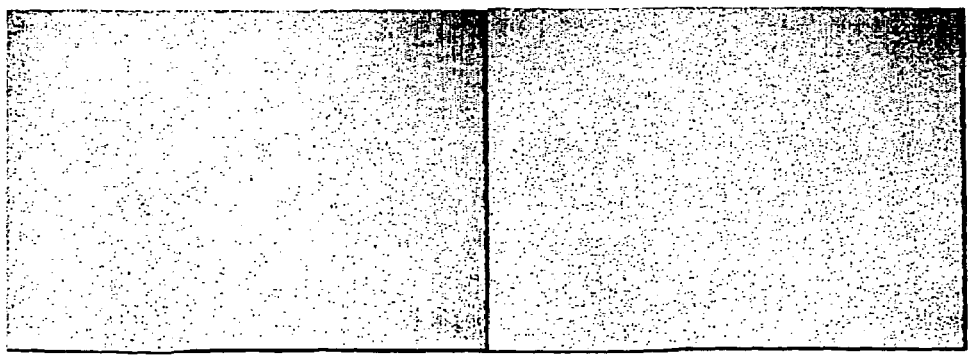
FIGS. 2a and 2b show images of gels observed.

Several tests have been performed with the on-line system based on the first and second configuration, with positive results (see FIGS. 2a and 2b). Gels look like typical polarisation-active objects composed of lighter and darker regions with poorly defined boundaries. Solid particles and fibres are also recognised with this method.

Figure 3:
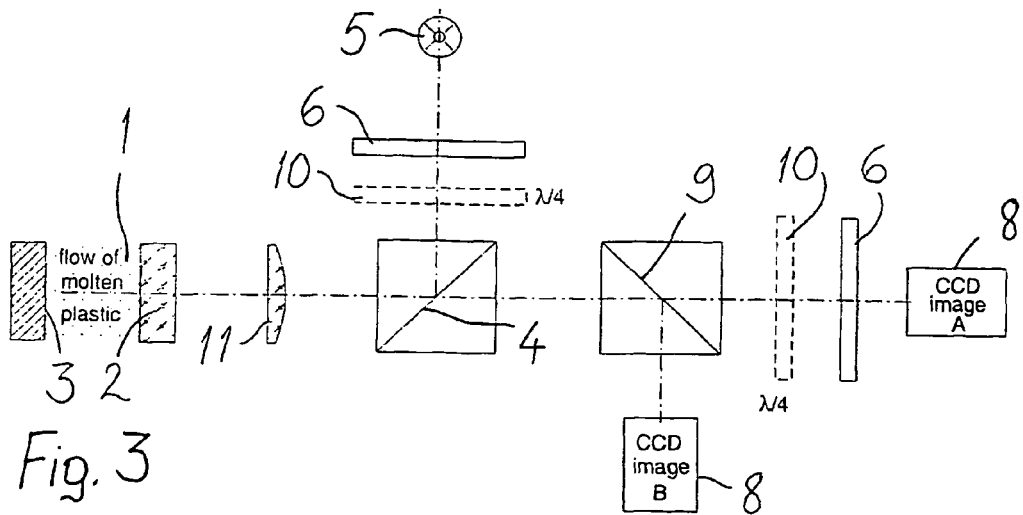
FIG. 3 shows a second embodiment of the invention.

An automated system should be able to identify impurities of different kinds and to determine a particle size distribution of impurities belonging to the specific type. Solid particles, fibres, non-melted crystals, as well as oxidised polymers can be identified e.g. by shape and transparency factor, but gels don't have clear boundaries and can be easily misinterpreted with solid particles which are out of focus. This problem can be solved, however, by utilising the fact that gels are visible only between crossed polarisers, but invisible when observed directly. In practice, this can be achieved by splitting light transmitted through the flow chamber 1 by a beam splitter 9 into two parts and forming simultaneously two images of the same event on two detectors 8, such as CCD cameras, as shown in FIG. 3. The basic arrangement is that of FIG. 1b, but the system of two detectors 8 and the light-splitting device can be applied to the arrangement of FIG. 1a as well. Image A will be formed with the help of a crossed analyser 7, while image B without it. Both images will be identical, with one exception: gels will be missing from the image B. With the help of a proper software one can now separate images of gels from images of solid-like impurities (image A–image B=gels only; image B=solids only), and classify properly types of inhomogeneities. If necessary, also shape recognition procedures can be used for additional justification and identification. Furthermore, particle size distribution can be calculated with already known algorithms.

Figure 1B:
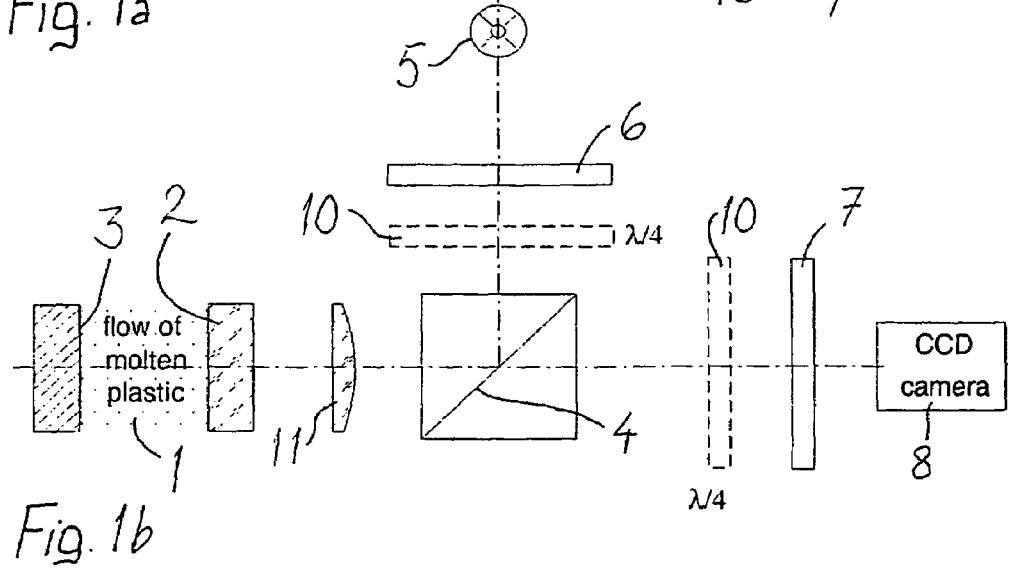

FIGS. 1a, 1b and 3 also show two quarter-wave plates ($\lambda/4$) 10 between the polarisers, in FIG. 1a on both sides of the flow and in FIGS. 1b and 3 on the same side of the flow. The arrangement where in the optical path there is a quarter-wave plate 9 after the light source 5 and the polarisator 6 transmits circularly polarised light through the flow of polymer melt. A lens in the optical path is denoted with 11.

The light source 5 means in this context a source of such electromagnetic radiation that can be polarised by the polarisator 6. Thus, the polarised electromagnetic radiation can be within any suitable wavelength range, such as visible or UV (ultraviolet), and it can be used continuously or in a pulsed manner, e.g. by using a flash lamp as the source of radiation.

The use of UV light, which need not be polarised, enables the contrast between the matrix and other phase objects by differences in spectral absorption properties of gels and the polymer matrix in a liquid state. Especially gels formed due to overheated parts in an extruder machine (burned particles) and highly cross-linked structures are visualised with higher contrast using UV light, the allowing secure automatic recognition of the objects by digital image processing. The use of a narrow band interference filter will suppress the visual wavelength of the light source thereby reducing straylight and increasing image sharpness of the objects in the melt stream. If the UV light is used for visualisation, the image capturing device (detector) should preferably be a back-illuminated CCD or a cheaper front-illuminated CCD which is coated with a UV-sensitive fluorescent layer.

According to one embodiment of the method using the UV light as the electromagnetic radiation passed through the liquid state polymer, the illumination of the flowing melt containing inhomogeneities is provided by a flash lamp, which delivers short light pulses (<10 $\mu$sec). The flash lamp may be free-running to act like a strobe illumination or triggered by the system electronics ccontrolled by a PC. The flash illumination provides high light intensity in short time, providing bright and sharp image quality for moving gels and specks in the melt. The flash lamp produces the necessary high intensive UV-light for enhancing contrast of gels.

In the alternative using a UV light emitting device as light source, both optical arrangements as shown in FIGS. 1a and 1b are possible, that is, the light source can be located on one side of the polymer flow chamber 1 and the detector on the other side thereof, or the light source and detector can be located onb the same side of the polymer flow chamber 1 and a reflector (mirror) for the light is used in the polymer flow channel. The polarisators can be omitted when a non-polarised UV light is used.

In addition to desired information from moving particles or gels, the image acquired by the image capturing device contains overlaid "background" information, which makes image processing more difficult or impossible. The main sources of image inhomogeneities or "background" are:
   non-uniform illumination of the scenery,
   imperfect optics,
   straylight or optical background,
   bad pixels and inhomogeneous sensitivity of the image capturing device,
   particles attached to windows.

In standard implementations, a correction is achieved by subtracting a "background" image from the acquired image. The acquired image usually contains the "background" information specified above, making automatic image processing extremely difficult. These image errors are removed if the "background" scenery of the acquired image and the reference "background" image are the same. The disadvantage of this procedure is that a different background image doubles the image errors, finally showing "background" scenery both from the acquired and from the background image after subtraction of the two images.

In many cases, the background scenery changes slowly with time and, to avoid image processing errors, a process of background measurement has to be performed at a certain image capturing rate. No impurity measurement is possible during background measurement and contamination particles may be missed during the measurement and calculation of the background image.

According to one embodiment of the present invention, the adaptive background correction avoids interrupting background measurement while, at the same time, allowing background compensation with a time-adaptive background image. In this way, all background inhomogeneities with a slow rate of change are removed automatically without interrupting the monitoring of the polymer melt, such as when monitoring an extrusion process, and without missing impurities due to an interrupting background measuring procedure.

The invention is characterised by subtracting a low-pass filtered background image based on the previously acquired images from the currently acquired image instead of taking a stationary background image. Many low-pass filter algorithms are well known for filtering real time signals. A filter algorithm is applied to successive intensity values from each image element (pixel) of the acquired sequence of images to obtain the "background" image. Filter parameters are selected to match the characteristics/rate of change of background variation and avoiding significantly influencing the resulting image. In a simple case, the "background" image is a moving average of n last images acquired (including or not including the current image). In this way, no additional images have to be acquired for background compensation. The main advantage of this procedure is that the "background" image is continuously updated with new background scenery by simply recalculating the "background image" using filter algorithms.

The invention of adaptive background subtraction is applicable both for continuous or pulsed illumination. Depending on the filter cut-off frequency or the number of sampled images, respectively, the low pass filtering of sampled images improves the quality or accuracy of the "background" image with respect to a stationary "background" image by reducing signal acquisition noise due to filtering.

Figure 4:
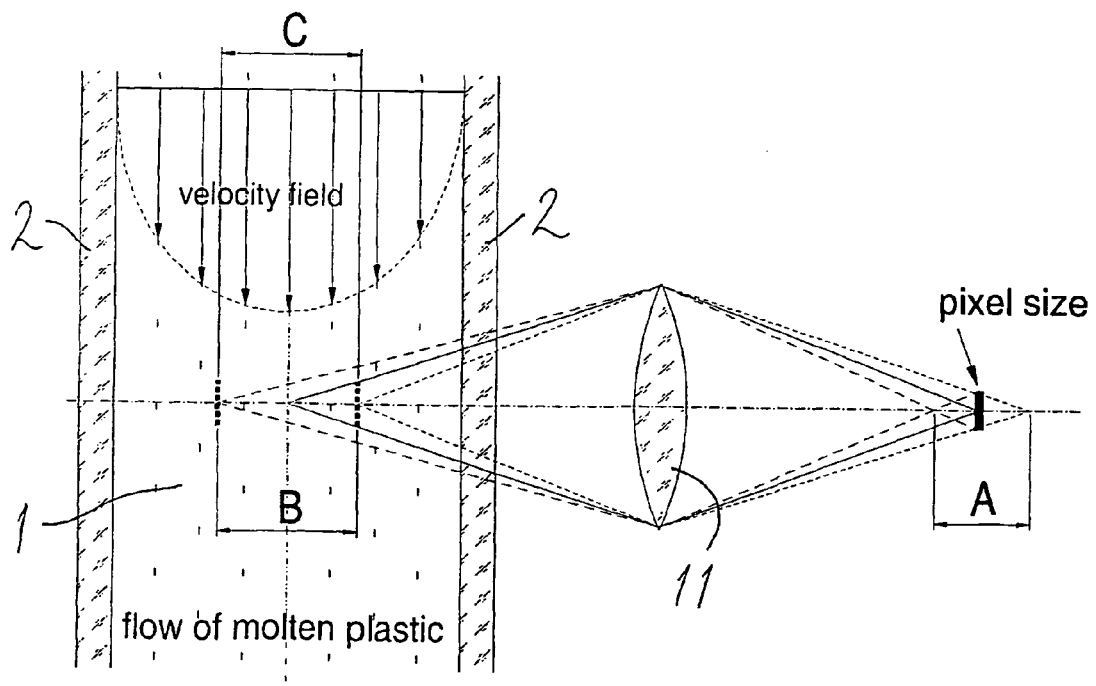
FIG. 4 shows a principle of still one embodiment of the invention.
Figure 5:
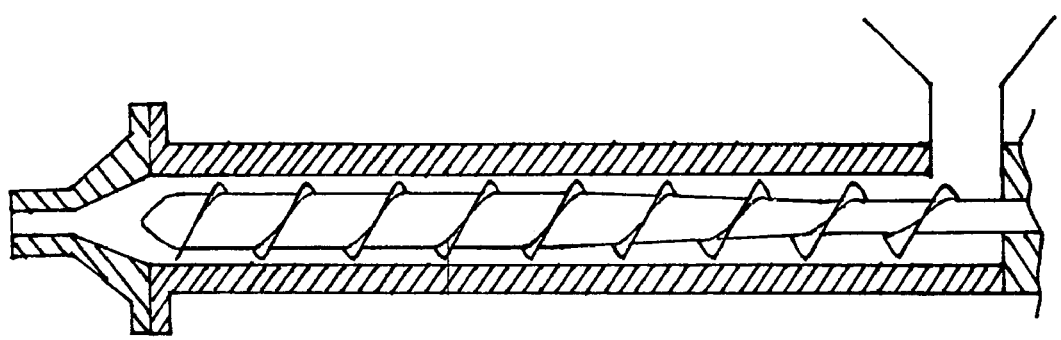
FIG. 5 shows a cross-sectional view illustrating the interior of an extruder or continuous kneader.

Additional difficulty in automatic calssification of detected objects may arise from misinterpretation between gels and particles being out of focus, as both produce images with low-contrast contours. Non-focused particles are observed always when the depth of field is lower (shorter) than the cross-section of a flow chamber, and this is usually the case when higher magnification or higher resolution is required. According to a further embodiment of the invention, a "velocity filter" can avoid erroneous classification of this kind by detecting the velocity of the particles and only considering particles which move within a certain "velocity window". The principle is explained in FIG. 4. A denotes the depth of focus in the image capturing device, B is the depth of field in the flow, and C denotes the velocity range corresponding to sharply imaged objects. The range is dependent on the velocity as a function of the cross sectional position of the object in the flow.

The flow chamber is assumed to force the passing material into a (near-) laminar flow, only showing small variations of the velocity vector with time at a specific location within the flow. On the other hand, pixel size of the image capturing device (the viewing camera) and the attached lens define the optical field of view and the depth of focus. A "velocity window" can be defined by matching the velocity profile inside the flow chamber with the depth of focus of the optical system applied.

In the invention, the "velocity window" is defined in a way which assures that all impurities which pass the velocity filter criterion are located within the space area which is imaged on the camera sensor within the depth of focus tolerances, i.e. with sufficiently good sharpness.

According to this invention, the velocity filter can implemented in the following manner:

A flash illumination is used, which can be triggered at sufficient rate to illuminate an acquired image twice or more times. The arrangement is set up in a way that the camera adequately images the path of travel of an impurity in the observation area at the time of the multiple flashes. This can be achieved by adjusting the delay between the flashes and by computer control of the image acquisition time period.

Alternatively, two or more images my be acquired, each with one flash illumination. Also, in this case, the effective period for velocity filtering is defined by the time between the flashes, not by the camera acquisition rate. Alternatively, a controlled shutter may be used with a continuous light source to generate similar images for velocity filtering. In this case, the effective period for velocity filtering is defined by the time period between the shutter opening events.

Preferably, the camera and the flash illumination or shutter are under full computer control and image acquisition is fully synchronised. In this case, adequate acquisition rates can be programmed to ensure that each impurity is only measured once and that a sufficient amount of material (or volume) is analyzed by matching the image acquisition rate to the flow velocity.

The velocity filter is easily implemented in software by identifying couples of similar objects with a specified distance vector tolerance. The tolerance of the distance vector can be estimated from the velocity profile of the melt in the flow chamber. Available digital image processing programs and libraries contain the required functions needed for object recognition. Only objects which pass the velocity criterion are considered by further image processing and counted and/or classified automatically to characterise the purity of the polymer material, such as extruded material.

The inspection point can be at the exit end of a liquid polymer flow channel, e.g. at a die with at least one of the side walls of the die made of material transparent to the electromagnetic radiation used. The die can be the exit end of an extruder for example. The flow of the polymer in a liquid state can also be monitored inside an extruder (single-screw or or multiple-screws) or continuous kneader, in the transition region between the screw(s) and die, or inside the die of an extruder or continuous kneader.

What is claimed is:

1. A method for monitoring of polymer in a liquid state to detect inhomogeneities therein, in which method the polymer in a liquid state flowing past an inspection point is monitored by forming an image, wherein at the inspection point, electromagnetic radiation in the form of UV light or polarized electromagnetic radiation is passed through the flow, and the absorption of the UV light or the changes in the state of polarization of the electromagnetic radiation caused by the inhomogeneities are used to observe them in the image formed, the measurement and classification of inhomogeneities being improved by selecting those objects that travel at a predetermined velocity in the flow, avoiding the measurement of unsharp objects due to small focal depth.

2. The method according to claim 1, wherein the velocity is determined by comparing image data obtained from the flow at predetermined intervals.

3. The method according to claim 2, wherein the image data is obtained by illuminating the flow at predetermined intervals.

4. The method according to claim 1, wherein the polymer in a liquid state is a polymer melt or resin.

5. The method according to claim 1, wherein the electromagnetic radiation is passed from one side of the polymer flow in a liquid state from a source of radiation, and received on the other side of the flow with a detector.

6. The method according to claim 1, wherein the electromagnetic radiation is passed from one side of the polymer flow in a liquid state from a source of radiation, and reflected from the other side back through the same flow further to a detector.

7. The method according to claim 1, wherein the electromagnetic radiation is passed through the flow as a pulse, which is recorded by a detector.

8. The method according to claim 1, wherein the inspection point is at the exit end of a polymer melt flow channel.

9. The method according to claim 1, wherein the flow of the polymer in a liquid state is monitored inside an extruder or continuous kneader, in a transition region between the screw(s) and die, or inside the die of an extruder or continuous kneader.

10. The method according to claim 1, wherein gel particles containing polymers with the same molecular composition as the matrix polymer are detected.

11. A method for monitoring of polymer in a liquid state to detect inhomogeneities therein, in which method the polymer in a liquid state flowing past an inspection point is monitored by forming an image, wherein at the inspection point, electromagnetic radiation in the form of UV light or polarized electromagnetic radiation is passed through the flow, and the absorption of the UV light or the changes in the state of polarization of the electromagnetic radiation caused by the inhomogeneities are used to observe them in the image formed, the flow of the polymer in a liquid state being monitored inside a single-screw or multiple-screw extruder or a continuous kneader, in the transition region between the screw(s) and a die, or inside a die of an extruder or continuous kneader.

12. The method according to claim 11, wherein the inspection point is at the die having side walls, at least one of the side walls of the die being made of material transparent to the electromagnetic radiation used.

13. The method according to claim 11, wherein the polymer in a liquid state is a polymer melt or resin.

14. A method for monitoring of polymer in a liquid state to detect inhomogeneities therein, in which method a matrix polymer in a liquid state flowing past an inspection point is monitored by forming an image, wherein at the inspection point, electromagnetic radiation in the form of UV light or polarized electromagnetic radiation is passed through the flow, and the absorption of the UV light or the changes in the state of polarization of the electromagnetic radiation caused by the inhomogeneities are used to observe them in the image formed, gel particles containing polymers with the same molecular composition as the matrix polymer being detected in the method.

15. The method according to claim 14, wherein the polymer in a liquid state is a polymer melt.

* * * * *